United States Patent
Junio et al.

(10) Patent No.: US 11,890,061 B2
(45) Date of Patent: Feb. 6, 2024

(54) GENERIC DEPTH INDICATOR FOR SURGICAL NAVIGATIONAL TOOLS

(71) Applicant: MAZOR ROBOTICS LTD., Caesarea (IL)

(72) Inventors: Dany Junio, Tel Aviv-Jaffa (IL); Kornelis Poelstra, Destin, FL (US)

(73) Assignee: MAZOR ROBOTICS LTD., Caesarea (IL)

( * ) Notice: Subject to any disclaimer, the term of this patent is extended or adjusted under 35 U.S.C. 154(b) by 376 days.

(21) Appl. No.: 16/958,275

(22) PCT Filed: Dec. 27, 2018

(86) PCT No.: PCT/IL2018/051405
§ 371 (c)(1),
(2) Date: Jun. 26, 2020

(87) PCT Pub. No.: WO2019/130314
PCT Pub. Date: Jul. 4, 2019

(65) Prior Publication Data
US 2020/0345430 A1    Nov. 5, 2020

Related U.S. Application Data

(60) Provisional application No. 62/610,516, filed on Dec. 27, 2017.

(51) Int. Cl.
| | |
|---|---|
| *A61B 34/20* | (2016.01) |
| *A61B 34/30* | (2016.01) |
| *A61B 90/00* | (2016.01) |
| *A61B 90/11* | (2016.01) |
| *B23B 49/00* | (2006.01) |
| *A61B 17/16* | (2006.01) |

(52) U.S. Cl.
CPC ............ *A61B 34/20* (2016.02); *A61B 34/30* (2016.02); *A61B 90/06* (2016.02); *A61B 90/11* (2016.02);
(Continued)

(58) Field of Classification Search
CPC ......... A61B 34/20; A61B 34/30; A61B 90/06; A61B 90/11; A61B 2034/2055;
(Continued)

(56) References Cited

U.S. PATENT DOCUMENTS

| | | |
|---|---|---|
| 5,409,493 A | 4/1995 | Greenberg |
| 5,732,703 A | 3/1998 | Kalfas et al. |

(Continued)

FOREIGN PATENT DOCUMENTS

| | | |
|---|---|---|
| GB | 2465631 | 6/2010 |
| WO | WO 2015/112566 | 7/2015 |

OTHER PUBLICATIONS

Extended Search Report for European Patent Application No. 18897084.2, dated Jan. 31, 2022, 8 pages.
(Continued)

*Primary Examiner* — Zade Coley
(74) *Attorney, Agent, or Firm* — Sheridan Ross P.C.

(57) ABSTRACT

A depth-indicating device for determining the depth of insertion of a surgical tool comprising a pair of spaced apart end caps, separated by a compressed spring, with the surgical tool passing through axial openings in both end caps, and firmly attached to one of the end caps, but free to slide through the opening in the other. A guide tube is attached to the second endcap, such that the surgical tool can be guided to its operating position on a body part. The second end cap and guide tube are attached to a location having a known position relative to the body part. A tracking marker is attached to the first end cap such that its longitudinal position can be tracked using a remote racking camera. Since the surgical tool is attached to the first end cap, the tool position is also tracked by the tracking system.

20 Claims, 2 Drawing Sheets

(52) U.S. Cl.
CPC ........ *B23B 49/005* (2013.01); *A61B 17/1615* (2013.01); *A61B 2034/2055* (2016.02); *A61B 2090/062* (2016.02); *A61B 2090/3937* (2016.02); *B23B 2260/0482* (2013.01)

(58) Field of Classification Search
CPC ...... A61B 2090/062; A61B 2090/3937; A61B 17/1615; B23B 49/005; B23B 2260/0482
See application file for complete search history.

(56) References Cited

U.S. PATENT DOCUMENTS

| | | | | |
|---|---|---|---|---|
| 6,887,247 | B1 * | 5/2005 | Couture | A61B 90/36 408/72 R |
| 7,165,336 | B2 | 1/2007 | Kim | |
| 9,198,698 | B1 | 12/2015 | Doose et al. | |
| 2005/0074304 | A1 * | 4/2005 | Couture | A61B 90/36 408/110 |
| 2009/0118742 | A1 * | 5/2009 | Hartmann | A61B 34/20 901/14 |
| 2011/0218546 | A1 * | 9/2011 | De la Fuente Klein | A61B 17/157 606/86 R |
| 2012/0211006 | A1 * | 8/2012 | Gill | A61B 34/30 128/200.26 |
| 2017/0071691 | A1 * | 3/2017 | Crawford | A61B 17/3423 |

OTHER PUBLICATIONS

International Search Report and Written Opinion prepared by the Israel Patent Office dated Apr. 1, 2019, for International Application No. PCT/IL2018/051405.

* cited by examiner

GENERIC DEPTH INDICATOR FOR SURGICAL NAVIGATIONAL TOOLS

CROSS REFERENCE TO RELATED APPLICATIONS

This application is a national stage application under 35 U.S.C. 371 and claims the benefit of PCT Application No. PCT/IL2018/051405 having an international filing date of 27 Dec. 2018, which designated the United States, which PCT application claimed the benefit of U.S. Provisional Patent Application No. 62/610,516 filed 27 Dec. 2017, the entire disclosures of each of which are incorporated herein by reference.

FIELD OF THE INVENTION

The present invention relates to the field of devices used in surgical navigation, especially minimally invasive procedures, for use in determining the insertion depth of a surgical tool.

BACKGROUND OF THE INVENTION

Depth indication is an important part of surgical navigation capability, allowing for the user to observe and be alerted to the current real-time depth of a surgical trajectory in comparison to patient anatomical landmarks. This capability is necessary especially in procedures in which the surgeon is operating under video-guided or other forms of indirect vision, to prevent as much as possible, depth-related errors. In minimally invasive procedures, the ability to accurately determine the depth of a surgical tool is important because of the practical inability to properly assess distance in a three dimensional scenario, without a proper line of sight. Errors in depth can easily cause irreversible disability or fatality, for example, in spinal procedures, by accidental insertion of sharp tools and implants beyond the vertebrae into the spinal cord or aorta.

A number of prior art navigational devices exist. Amongst such devices, U.S. Pat. No. 5,409,493 to Greenberg for "Single-handed Surgical Drill Depth Guide" discloses a device, specifically for treating fractures in the craniomaxillofacial region. The depth gauge is used to determine the correct screw length during a fixation procedure. U.S. Pat. No. 7,165,336 to Kim for "Surgical Depth Instrument" describes a device for measuring the depth of a hole in a bone having a digital readout for providing measurements to the operator. Both of these devices are handheld tools with specific and limited uses. WO 2015/112566 filed by Conformis Inc., for "Spring-fit Surgical Guides" describes a block-shaped spring-fit tool guide that may include depth detection, designed to assist in tool alignment during joint implant procedures. U.S. Pat. No. 9,198,698 to Doose et al. for "Minimally Invasive Spinal Fixation System and Related Methods" discloses a minimally invasive spinal fixation system with guides and instruments for aiding in insertion and positioning of rods during a spinal fixation operation.

U.S. Pat. No. 5,732,703 to Kalfas et al. for "Stereotaxy Wand and Too Guide" discloses a device connected to a navigation system. The system comprises a series of light emitters on the wand that are detected by a set of CCD camera receivers. A calibration procedure is required to align the wand with the remote detection system, after which the wand, in combination with a tool guide, can be used to plan a tool trajectory. The wand-tool guide component of the system is designed to be handheld by the operator.

Several problems exist with current navigational devices, leaving the field with a need for a solution that rectifies these deficiencies. One problem is the need for calibration. With some surgical navigation systems, every tool must be individually calibrated before each use. Not only is this technical verification process time-consuming—it is also prone to human error. A second difficulty is that in many prior art systems, a positional marker is attached to the tool and viewed by an associated navigation system. If the marker moves out of view of the camera because the tool was rotated by the operator or positioned behind another object, the tool will lose connection with the remote navigation system and thus cease to preserve its relative position, thereby losing its ability to indicate depth. Finally, with current surgical navigation systems, the process of tool calibration is generally limited to designated tools compatible with a given navigation system. A surgeon using a certain navigation system may prefer or need to use a tool of a different company with different or incompatible navigation markers, or even may wish or need to use a tool that is not compatible with any marker at all.

Therefore, there exists a need for an intra-operative depth indicator and tool guide which overcomes at least some of the disadvantages of prior art systems and methods.

The disclosures of each of the publications mentioned in this section and in other sections of the specification, are hereby incorporated by reference, each in its entirety.

SUMMARY

The present disclosure describes a new exemplary generic intra-operative depth indicator device for determining the depth of insertion of a surgical tool, that is not limited to a specific navigation or tracking system or to a specific manufacturer and which requires no pre-calibration when used on a platform such as a surgical robotic arm, or a fixed mounting position.

The device comprises three basic components—a pair of spaced apart end caps, conveniently in the form of thin plate-like elements, which are kept separated by a compressed spring. The surgical tool passes through axial openings in both end caps, and is firmly attached to a first one of the end caps, but free to slide through the opening in the second. A guide tube is advantageously attached to the second end cap, such that the surgical tool passing through the opening in the second end cap can be accurately guided to its operating position on a body part. This second end cap and guide tube are attached to a location having a known position relative to the body part. A tracking marker is attached to the first end cap such that its longitudinal position relative to the second cap fixed to the location having a known position relative to the body part, can be tracked using a remote navigation or tracking camera, as part of a navigation or tracking system. Since the surgical tool is firmly attached to the first end cap, the tool position relative to the body part is also tracked by the tracking system, and hence also the operating end of the tool, whose depth of entry into the body part, the device it is intended to monitor. The tracking marker is mounted on a rotating arm, allowing the marker to rotate freely in 360 degrees around the device axis, such that a clear tracking line of sight can be obtained regardless of obstructions generated during the surgical procedure.

There is therefore provided according to a first exemplary implementation of the devices described in this disclosure, a device for determining the depth of insertion of a surgical tool, the system, comprising:

(i) a first and a second cap element, each cap having an axial opening adapted for insertion of the surgical tool, the surgical tool being fixed in the axial opening in the first cap element and freely movable through the opening in the second cap element, (ii) a compressed spring extending between the first and second cap elements, (iii) a tool guide attached to the second cap element, and (iv) a first position marker attached to the first cap element, such that the position of the first cap element can be determined in a remote tracking system, wherein the second cap element is disposed at a location whose spatial position is known.

In such a depth-indicating device, the location may be the end effector of a robotic arm. In such a case, the position of the end effector of the robotic should be correlated with the remote tracking system, such that the depth indicating device provides a correct indication of the position of the tool taking into account any motion of the end effector.

Alternatively, the location may be a fixed support in the region of a body part on which the surgical tool is to operate. The spatial location of a body part on which the surgical tool is to operate may be known to the remote tracking system.

Any of the above described devices may further comprise a second position marker attached to the second cap element, or to a component having a known spatial relation to the second cap element, such that the spatial position of the second cap element can be determined in the remote tracking system.

Furthermore, in any of the above described devices the first position marker may be attached to the first cap element, such that it can freely rotate about the axis of the cap element, such that if the line of sight between the first position marker and the remote tracking system is obstructed, the first position marker can be rotated to a different orientation, and the position of the first cap element can be determined using aid first position marker in the different orientation.

Additionally, in such devices the spring may have a free length such that it remains compressed when the first and the second cap elements are separated by their maximum intended distance. Also, the spatial position of the location may be known to the tracking system.

Finally, according to any of the previously described depth-indicating devices, the spatial position of the location may be known relative to the body part on which the surgical tool is to operate by means of the remote tracking system and a marker element mounted in a known location relative to the anatomical body part. As an alternative, the spatial position of the location may be known relative to the body part on which the surgical tool is to operate by means of a registration procedure involving anatomical comparisons using intraoperative images.

The terms tracking and navigation, are used interchangeably in the present application, and are understood to mean the ability to determine the pose (position and orientation) of an object being tracked or navigated.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
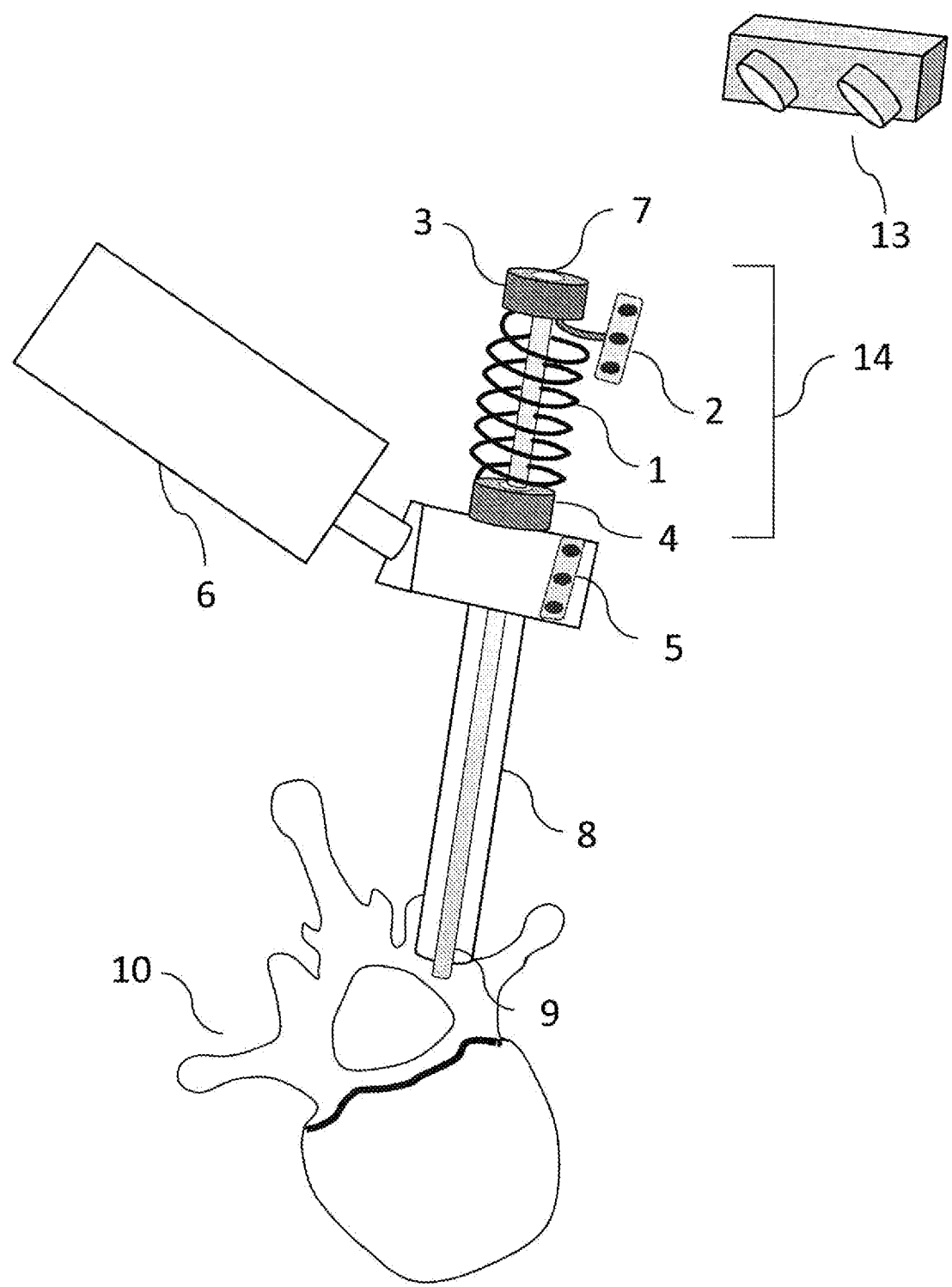
FIG. 1 shows a schematic view of an implementation of the invention using the generic spring depth control navigation device to measure the depth of entry of a surgical drill bit into a vertebral body.

Reference is now made to FIG. 1, which illustrates schematically one example of the generic depth indicator of the present disclosure. A spring 1 is contained between end caps 3, 4 by each of its ends. The unloaded length of the spring must be greater than the maximum distance between the end caps 3, 4, in order to always maintain the spring in a minimally compressed state end, such that the end caps 3, 4, are always at a clearly defined distance apart, for any normal mutual position of the end caps. The proximal end cap 3, contains an opening 7 into which a surgical tool 9 can be inserted and attached to the end cap 3, such that the cap moves with motion of the tool, or vice versa. The term proximal is used throughout this disclosure to relate to that end of an element closer to the operator, while the term distal relates to the end closer to the subject. To the proximal cap is attached a navigation marker 2, which can optionally rotate around the axis of the device through 360 degrees. The function of this marker will be described hereinbelow. The distal cap 4 also has an opening 17, through which the surgical tool 9 can freely slide, and this cap acts as an anchoring cap in that it is attached or anchored to a position whose location in space is defined relative to the anatomic body part on which the tool is to operate. This position could be either a fixed position, or the end effector of a robotic arm 6, whose position in space relative to the anatomic element is defined by the robotic control. The pose of the end effector of the robotic arm should be known relative to the subject's anatomy—in the example shown, a spinal vertebra 10—by any of the methods known in the art, whether by means of three dimensional navigation markers, or by using a registration procedure for defining the pose of the robotic arm relative to the bone using intraoperative images.

In addition, a tool guide 8 is also attached to the fixed reference position, or the end effector of the robotic arm 6, together with the anchor cap 4, such that the surgical tool 9 passes through the opening 17 in the anchoring cap 4, and down the tool guide 8, as is known in the art. The tool guide may have a serrated distal end (not shown) for gripping a bone onto which it is aligned, to prevent skiving. The end caps 3, 4, and the spring 1 together comprise a depth indicator 14. The surgical tool 9 is inserted through the depth indicator 14, which is attached to the fixed reference position or to the robotic arm 6 from above, and through the tool guide 8 which is also attached to the fixed reference position or the robotic arm 6.

Actuation of the depth indicator occurs when the surgical tool 9, a bone drill in the exemplary implementation shown in FIG. 1, is advanced by the surgeon. Since the surgical tool is firmly clamped to the end cap 3, longitudinal motion of the surgical tool 9 results in corresponding longitudinal motion of the end cap 3, thereby compressing the spring 1 of the depth indicator 14 between the proximal end cap 3 and the distal end cap 4, which is held in the robotic arm. The spring may be physically connected to the end caps 3, 4, or simply retained therebetween by the compression of the spring. The position of the proximal end cap 3 is monitored by means of a navigation system, which can determine the position of a marker element 2 attached to the end cap. A navigational tracking camera 13 is shown remotely positioned in a location where it can surveille the operating region, and determine the three dimensional position and orientation of any navigation markers in the surveillance region. The displacement of the marker element 2 relative to the fixed location of the distal end cap 4, is measured by the navigation system. That displacement can alternatively be determined by means of one or more additional marker elements 5 attached in a fixed position relative to the distal end cap 4, whose position can be determined by the same navigation system 13 as that used to determine the position of the proximal, moving end cap 3. The depth indicator is thus able to determine the linear longitudinal displacement of the surgical tool 9 affixed to the proximal ends cap 3, and hence, from a knowledge of the starting point of the end tip of the tool, the displacement of that end tip as the surgeon proceeds with the insertion procedure.

Figure 2:
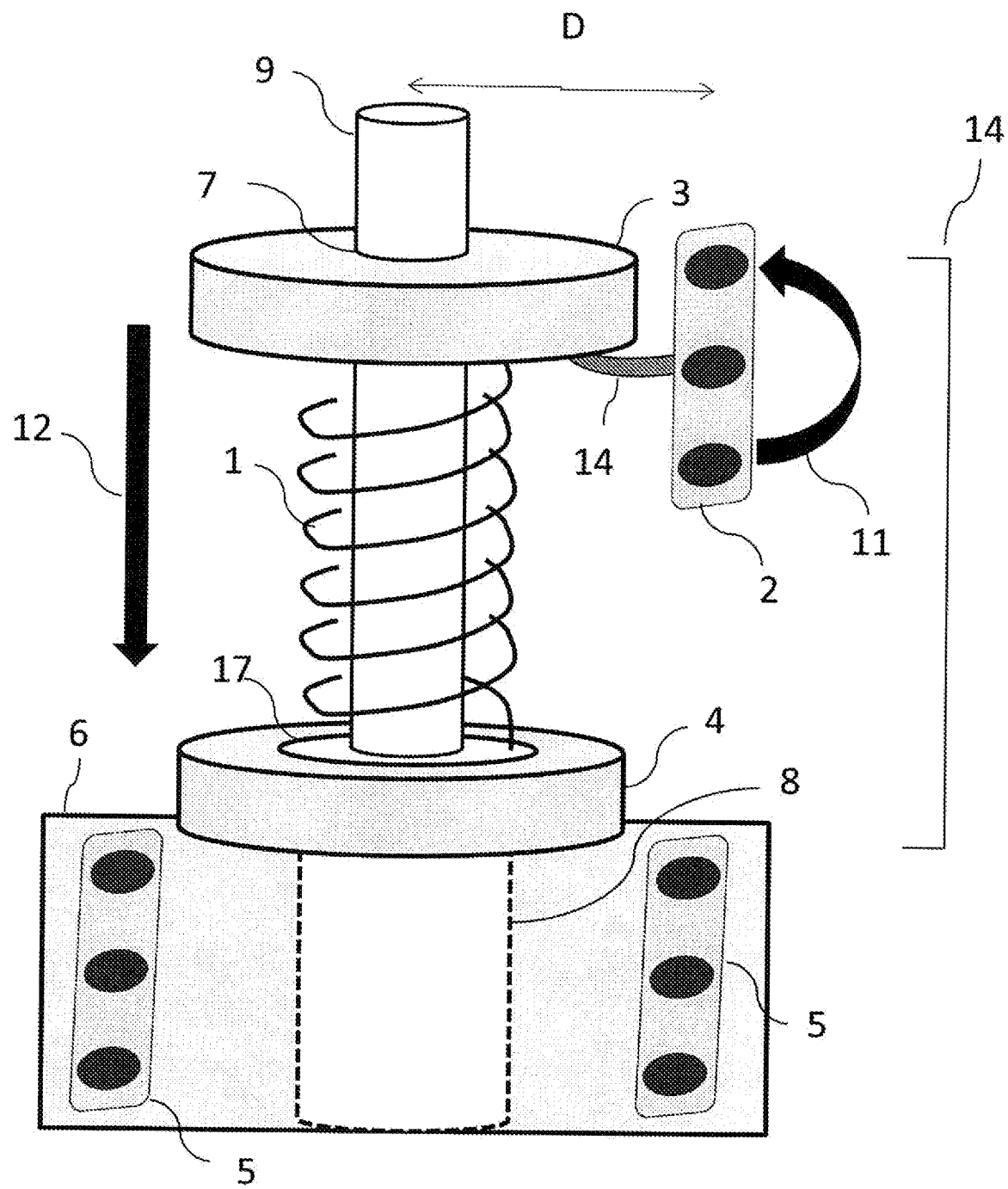
FIG. 2 shows details of the depth indicator in operation and its connection to a robotic arm

Reference is now made to FIG. 2, which is a schematic close-up view of the depth indicator 14. A surgical tool 9 is shown inserted through the opening 7 in the distal cap 3 of the device, to which it is firmly attached. The surgical tool 9 extends through the spring 1, the opening 7 in the proximal cap 4, and the tool guide 8, which is attached to the fixed reference position, or to the robotic arm 6. The fixed reference position, or the position of the robotic arm used for holding the depth indicator at its distal end cap, may be equipped with navigational markers 5, such that their location is known to the navigation system. As the surgical tool 9 is advanced by the surgeon into the bone, the proximal end cap 3 also moves distally with the drill, thus compressing the spring in a linear direction 12, and this distal linear movement of the markers 2 attached to the end cap is detected by the navigation system, which can thus provide a measure of the distal movement of the tool tip.

Since navigation markers 2 may be obscured by the device as the linear longitudinal motion 12 proceeds, or as the surgeon moves his hands, the marker may be attached to the proximal endcap in a manner that allows it to rotate 11 around the axis of the device, such that if one particular position shields the navigational line of sight, the marker may be rotated until visual line of sight contact is again made with the navigation system detector camera 13. In the example shown in FIG. 2, the marker element 2 is attached by means of an arm 14 to a rotary bearing (not shown) attached to the axis of the device at the end plate 3, such that the marker element can rotate freely around the device axis, and at a known distance D therefrom. The marker 2, has a three-dimensional layout, whose configuration is known. That configuration defines a known axis, and a known plane of the marker. In the example marker shown in FIG. 2, the marker element has a linear form whose length axis is perpendicular to the plane of rotation of the marker element around the axis of the depth indicator, and hence is parallel to the axis of the tool, and a fixed distance D away therefrom. The navigational system to able to determine, from the three dimensional configuration of the marker element, its angular rotational position relative to the alignment of the depth indicator, and its distance from the axis is known, such that the longitudinal position of the tool can be determined regardless of the rotational position of the marker. Thus, the marker can be freely rotated to avoid obstruction of the line of sight, and still is able to track the longitudinal insertion of the tool.

When use is made of a tool not having angular symmetry, there is a need to relate the rotational position of the tool with the depth indicator, such that the orientational detection mode of the navigation system can relate to the correct orientation of the tool as the marker is swung around the tool axis. This can be achieved by providing a directional indication in the end plate or another part of the depth indicator, such as a longitudinal slot, which interfaces with a matching feature on the tool, such that the tool orientation is known to the navigational system and to the angular position of the rotating marker.

The described device has advantages over prior art devices. First, having its own navigation markers operable through 360 degrees, enables it to be fully functional for depth detection in any position. Further, as the device is independent of need for calibration, it saves time and eliminates the error range incumbent in human-dependent procedures. It can be used with any robotic arm or navigation system. The device is designed to be used in combination with a fixed tool guide and does not need to be removed or exchanged with the tool guide in order to operate the tool.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system, comprising:
    a depth-indicating device for determining a depth of insertion of a surgical tool;
    a first element and a second element, each element having an axial opening adapted for insertion of the surgical tool, such that, after insertion, the surgical tool is fixed in the axial opening in the first element and freely movable through the axial opening in the second element;
    a compressible spring extending between the first element and second element;
    a tool guide attached to the second element;
    a first position marker attached to an outside surface of the first element and configured to rotate about an axis of the first element, such that a position of the first element can be determined in a tracking system remote from the depth-indicating device; and
    a robotic system having a robotic arm configured to support the second element,
    wherein the second element is configured to be disposed at a location whose spatial position is known to the robotic system or to the tracking system, and
    wherein the depth of insertion of the surgical tool is determined based, at least in part, on a movement or position of the first element relative to the second element.

2. The system of claim 1, wherein the second element is connectable to an end effector at an end of the robotic arm.

3. The system of claim 2, wherein a position of the end effector of the robotic system is correlated with the tracking system, such that the depth-indicating device provides an indication of a pose of the surgical tool taking into account any motion of the end effector.

4. The system of claim 1, wherein the second element is attached to a fixed support in a region of a body part on which the surgical tool is to operate.

5. The system of claim 1, wherein a spatial location of a body part on which the surgical tool is to operate is known to the tracking system.

6. The system of claim 1, further comprising a second position marker attached to the second element or to a component having a known spatial relation to the second element, such that a spatial position of the second element can be determined in the tracking system.

7. The system of claim 1, wherein the first position marker is attached to the first element such that the first position marker can freely rotate about an axis of the first element while the first element remains fixed, such that if a line of sight between the first position marker and the tracking system is obstructed, the first position marker can be rotated to a different orientation, and a pose of the first element can be determined using the first position marker in the different orientation.

8. The system of claim 1, wherein the first element and second element have a maximum separation distance and wherein the compressible spring has a free length such that the compressible spring remains compressed when the first element and the second element are separated by the maximum separation distance.

9. The system of claim 1, wherein the spatial position of the second element is known to the tracking system.

10. The system of claim 1, wherein a pose of the second element is known relative to a body part on which the surgical tool is to operate, by the tracking system and a marker element mounted in a known location relative to the body part.

11. The system of claim 1, wherein a pose of the second element is known relative to a body part on which the surgical tool is to operate by a registration procedure involving anatomical comparisons using intraoperative images.

12. The system of claim 1, wherein the first element moves with the surgical tool.

13. A tracking device for a robotic surgical arm having an end effector, the tracking device comprising:
  a first depth detector member configured to securely engage a first portion of a surgical tool passing through the end effector of the robotic surgical arm, the first depth detector member including an optical tracker attached to an outside surface of the first depth detector member, configured to rotate relative to the first depth detector member, and configured to provide location information to a remote tracking system;
  a second depth detector member configured to slidingly engage a second portion of the surgical tool, the second depth detector member being configured to be secured at a fixed location relative to the end effector of the robotic surgical arm; and
  a resilient member extending between the first depth detector member and the second depth detector member,
  wherein a depth of insertion of the surgical tool is determined based, at least in part, on a movement or position of the first depth detector member relative to the second depth detector member.

14. The tracking device of claim 13, further comprising a tool guide attached to the second depth detector member.

15. The tracking device of claim 13, wherein a pose of the second depth detector member is known relative to a body part on which the surgical tool is to operate, by the remote tracking system and a marker element mounted in a known location relative to the body part.

16. The tracking device of claim 13, wherein a pose of the second depth detector member is known relative to a body part on which the surgical tool is to operate by a registration procedure involving anatomical comparisons using intraoperative images.

17. The tracking device of claim 13, wherein the optical tracker is configured to selectively rotate about an axis of the first depth detector member while the first depth detector member remains fixed, such that if a line of sight between the optical tracker and the remote tracking system is obstructed, the optical tracker can rotate to a different orientation and a pose of the first depth detector member can be determined using the optical tracker in the different orientation.

18. The tracking device of claim 13, wherein the first depth detector member moves with the first portion of the surgical tool.

19. A tracking device for a surgical system having an end effector, the tracking device comprising:
  a first depth detector member configured to securely engage a first portion of a surgical tool, the first depth detector member including an optical tracker attached to an outside surface of the first depth detector member, configured to rotate about an axis of the first depth detector member, and configured to provide location information to a remote tracking system;
  a second depth detector member configured to slidingly engage a second portion of the surgical tool, the second depth detector member supported by a robotic arm, the second depth detector member being configured to be disposed at a location whose spatial position is known relative to a body part on which the surgical tool is to operate; and
  a resilient member extending between the first depth detector member and the second depth detector member,
  wherein a depth of insertion of the surgical tool is determined based, at least in part, on a movement or position of the first depth detector member relative to the second depth detector member.

20. The tracking device of claim 19, wherein the first depth detector member moves with the first portion of the surgical tool.

* * * * *